(12) United States Patent
Lu et al.

(10) Patent No.: US 11,390,614 B2
(45) Date of Patent: Jul. 19, 2022

(54) METHOD FOR PREPARING BENZOFURAN DERIVATIVE

(71) Applicants: JIANGSU HENGRUI MEDICINE CO., LTD., Lianyungang (CN); SHANGHAI HENGRUI PHARMACEUTICAL CO., LTD, Shanghai (CN)

(72) Inventors: Weidong Lu, Shanghai (CN); Chao Xu, Shanghai (CN); Haoyu Zhang, Shanghai (CN); Qiyun Shao, Shanghai (CN); Jun Feng, Shanghai (CN); Feng He, Shanghai (CN)

(73) Assignees: JIANGSU HENGRUI MEDICINE CO., LTD., Lianyungang (CN); SHANGHAI HENGRUI PHARMACEUTICAL CO., LTD., Shanghai (CN)

( * ) Notice: Subject to any disclaimer, the term of this patent is extended or adjusted under 35 U.S.C. 154(b) by 133 days.

(21) Appl. No.: 16/762,795

(22) PCT Filed: Nov. 9, 2018

(86) PCT No.: PCT/CN2018/114798
§ 371 (c)(1),
(2) Date: May 8, 2020

(87) PCT Pub. No.: WO2019/091450
PCT Pub. Date: May 16, 2019

(65) Prior Publication Data
US 2021/0188822 A1     Jun. 24, 2021

(30) Foreign Application Priority Data
Nov. 10, 2017  (CN) .......................... 201711104888.3

(51) Int. Cl.
*C07D 405/14*     (2006.01)
*C07C 51/363*     (2006.01)

(52) U.S. Cl.
CPC .......... *C07D 405/14* (2013.01); *C07C 51/363* (2013.01)

(58) Field of Classification Search
CPC .......................... C07D 405/14; C07C 51/363
See application file for complete search history.

(56) References Cited

U.S. PATENT DOCUMENTS

| | | |
|---|---|---|
| 3,236,625 A | 2/1966 | Klein et al. |
| 5,344,968 A | 9/1994 | Lilitkarntakul et al. |
| 6,211,203 B1 | 4/2001 | Amschler |
| 6,331,556 B2 | 12/2001 | Dyke et al. |
| 7,057,067 B2 | 6/2006 | Kodama et al. |
| 8,846,935 B2 | 9/2014 | Duquenne et al. |
| 9,018,382 B2 | 4/2015 | Duquenne et al. |
| 10,017,500 B2 | 7/2018 | Kanno et al. |
| 2003/0181759 A1 | 9/2003 | Kodama et al. |
| 2004/0034047 A1 | 2/2004 | Burri et al. |
| 2009/0131688 A1 | 5/2009 | Burgos et al. |
| 2013/0053383 A1 | 2/2013 | Duquenne et al. |
| 2014/0350013 A1 | 11/2014 | Duquenne et al. |
| 2017/0073335 A1 | 3/2017 | Kanno et al. |
| 2018/0282313 A1 | 10/2018 | Kanno et al. |
| 2018/0327394 A1 | 11/2018 | Lu et al. |

FOREIGN PATENT DOCUMENTS

| | | | |
|---|---|---|---|
| CN | 1426388 A | 6/2003 | |
| CN | 101434582 A | 5/2009 | |
| WO | 2011140325 A1 | 11/2011 | |
| WO | 2012142513 A1 | 10/2012 | |
| WO | 2013039988 A1 | 3/2013 | |
| WO | 2015141616 A1 | 9/2015 | |
| WO | 2017084494 A1 | 5/2017 | |
| WO | WO 2017/084494 | * 5/2017 | ......... A61K 31/4433 |

OTHER PUBLICATIONS

Tabata Hidetsugu et al: "A Complete Gear System in N-Benzoyl-Carbazole Derivatives", Organic Letters., [Online] vol. 16, No. 5, Feb. 24, 2014 (Feb. 24, 2014), pp. 1514-1517, XP055808348, us ISSN: 1523-7060, DOI: 10.1021/ol500417t Retrieved from the Internet: URL:https://pubs.acs.org/doi/pdf/10.1021/o 1500417t> [retrieved on May 27, 2021] * Scheme 1; Citation 4 *.

Tabata Hidetsugu et al: "Supporting Information a Complete Gear System in N-Benzoyl-Carbazole Derivatives", Organic Letters, Feb. 14, 2014 (Feb. 14, 2014), pp. S0-S45, XP055808305, Retrieved from the Internet: URL:https://pubs.acs.org/doi/full/10.1021/ ol500417t [retrieved on May 27, 2021] * p. SI, paragraph 2., compound SI *.

The office action for a counterpart Taiwan application No. 107139895 dated Sep. 4, 2019 as well as its English Translation.
The office action for a counterpart Taiwan application No. 107139895 dated Feb. 5, 2020 as well as its English Translation.
The office action for a counterpart Taiwan application No. 107139895 dated Jun. 3, 2020 as well as its English Translation.
Twiss and Heinzelmann, "The Oxidation of Iodinated Phthalic and Benzoic Acids", The Journal of Organic Chemistry, 1950, pp. 496-510.

* cited by examiner

*Primary Examiner* — Erich A Leeser
(74) *Attorney, Agent, or Firm* — Harness, Dickey & Pierce, P.L.C.

(57) ABSTRACT

Disclosed is a method for preparing a benzofuran derivative. In particular, provided is a method for preparing a benzofuran derivative, wherein according to the method provided, reaction steps required to synthesize the benzofuran substance in the prior art can be effectively shortened.

6 Claims, No Drawings

METHOD FOR PREPARING BENZOFURAN DERIVATIVE

The present application is a 371 National Phase of International Application No. PCT/CN2018/114798, filed on Nov. 9, 2018, which claims the benefit of Chinese patent application NO: CN201711104888.3 filed on Nov. 10, 2017. The entire disclosures of the above applications are incorporated herein by reference in their entirety.

FIELD OF INVENTION

The present invention relates to a method for preparing a benzofuran derivative.

PRIOR ARTS

Lymphoma is a malignant tumor originating in the lymphoid hematopoietic system. It is divided into two categories, non-Hodgkins lymphoma (NHL) and Hodgkins lymphoma (HL) according to the difference of tumor cells. 90% of the patients in Asia are NHL, and pathologically they are mainly lymphocytes, histiocytes or reticulocytes with various degrees of differentiation. According to the natural history of NHL, this category can be classified into three major clinical types: highly invasive lymphoma, invasive lymphoma and indolent lymphoma. According to the origin of different lymphocytes, it can be divided into B cell lymphoma, T cell lymphoma and natural killer (NK) cell lymphoma, wherein the main function of B cell is to secrete various antibodies to help the body resist various invasions.

Histone methyltransferase encoded by EZH2 gene is a catalytic component of polycomb repressive complex 2 (PRC2). Compared with normal tissues, expression level of EZH2 is abnormally elevated in cancer tissues, while the expression level of EZH2 is highest in advanced cancer or poor prognosis of cancer. In some cancer types, overexpression of EZH2 occurs simultaneously with amplification of gene encoding EZH2. A large number of si/shRNA experiments have found that reducing expression of EZH2 in tumor cell lines can inhibit the proliferation, migration and invasion or angiogenesis of tumor cells, and lead to apoptosis.

Currently, there are EZH2 inhibitors that have entered the stage of clinical development. The following is a brief list: Tazemetostat (EPZ-6438) developed by Eisai for treatment of non-Hodgkin B-cell lymphoma is currently in the clinical phase II. CPI-1205 developed by Constellation for treatment of B-cell lymphoma is currently in the clinical phase I. GSK-2816126 developed by GlaxoSmithKline for treatment of diffuse large B-cell lymphoma and follicular lymphoma is currently in the clinical phase I

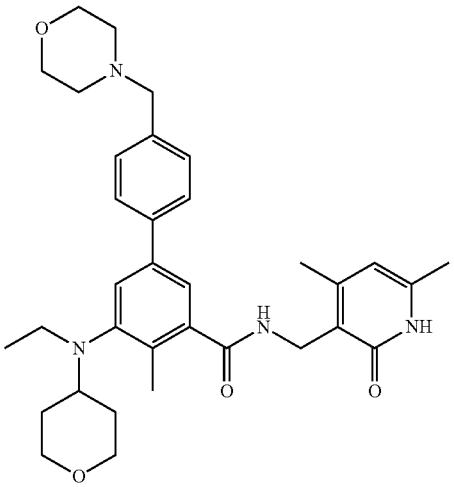

EPZ-6438

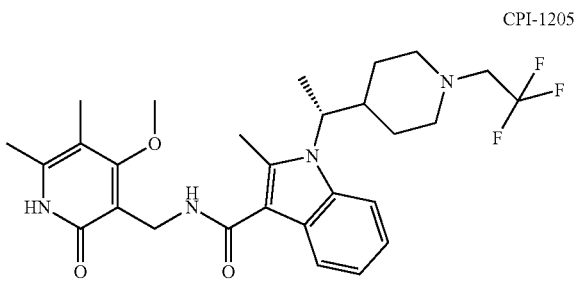

CPI-1205

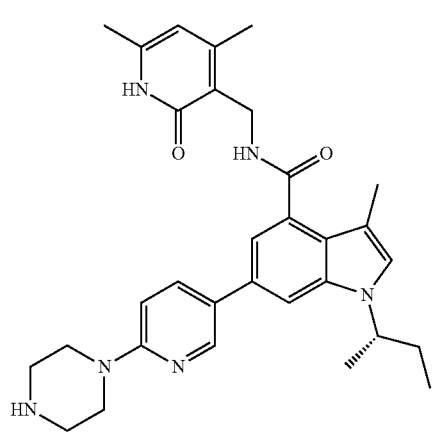

GSK-2816126

PCT application WO2017084494A provides an EZH2 inhibitor with the following structure:

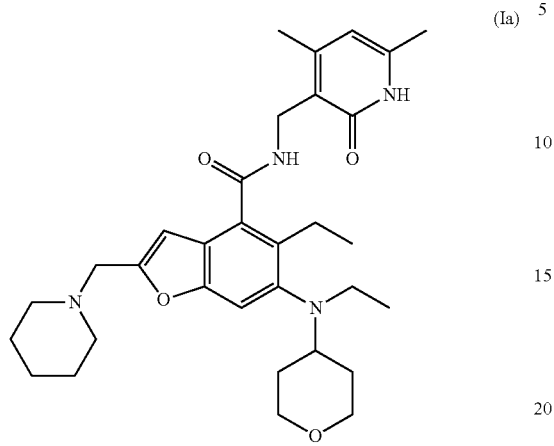

(Ia)

This application also discloses a method for preparing compound Ia, however, the method disclosed in this application requires up to fourteen steps (as shown in Scheme1), and there is potential safety hazards with nitrification, bromination and the fourth step of diazonium salt hydrolysis of the scheme; the two-step reaction is regioselective, and isomers are not easy to separate and purify; many steps in the preparation process require column chromatography, which is not suitable for industrial production. Therefore, simplification of the synthesis of the substance and shortening the corresponding reaction steps are still of research value.

Scheme 1

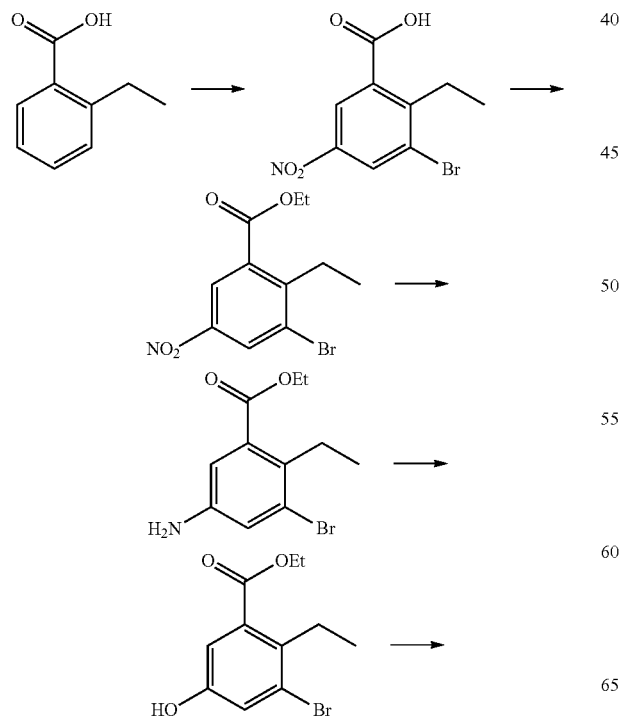

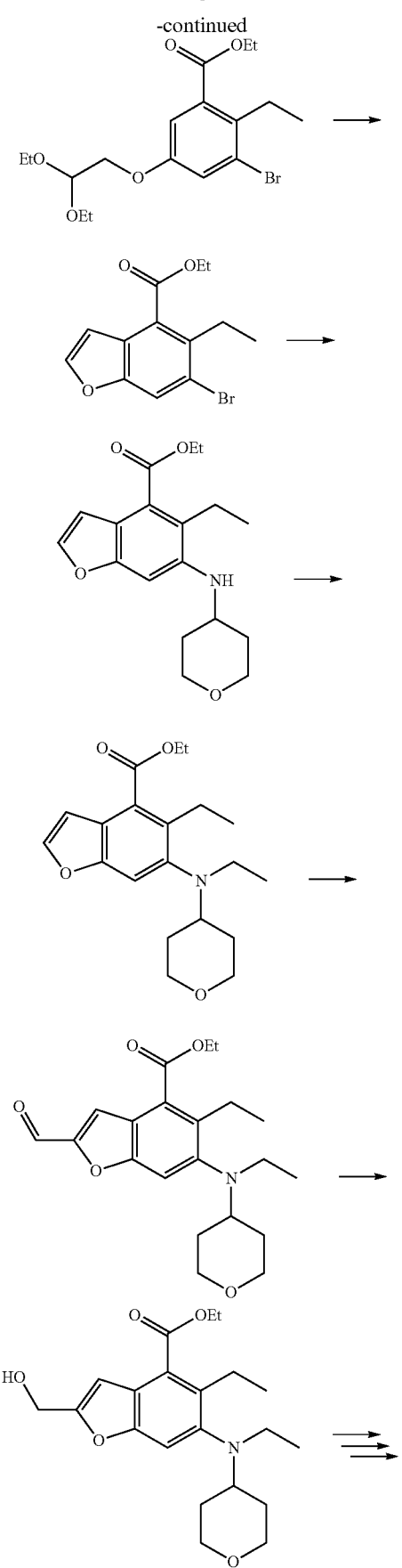

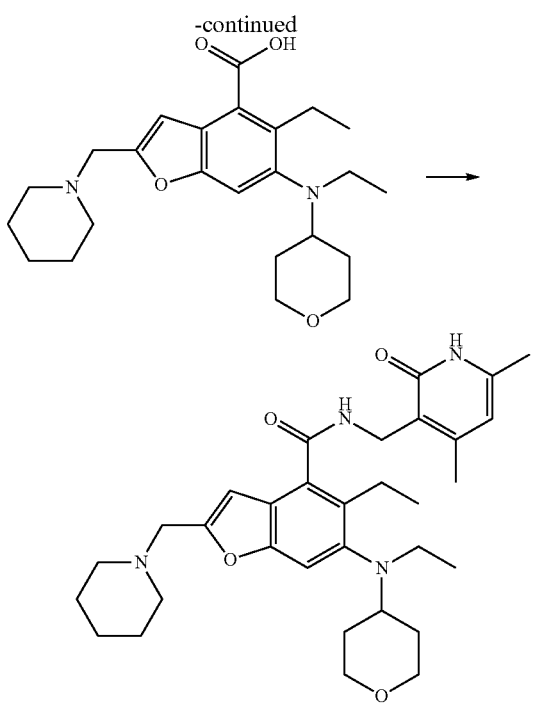

Content of the Present Invention

The present invention provides a novel method for preparing a benzofuran derivative. The method provided by the present invention can significantly shorten the steps for preparing a benzofuran derivative.

The present invention provides a method for preparing a benzofuran derivative represented by formula IV, wherein a compound represented by formula IV is prepared by reacting of a compound represented by formula VI with a compound represented by formula V,

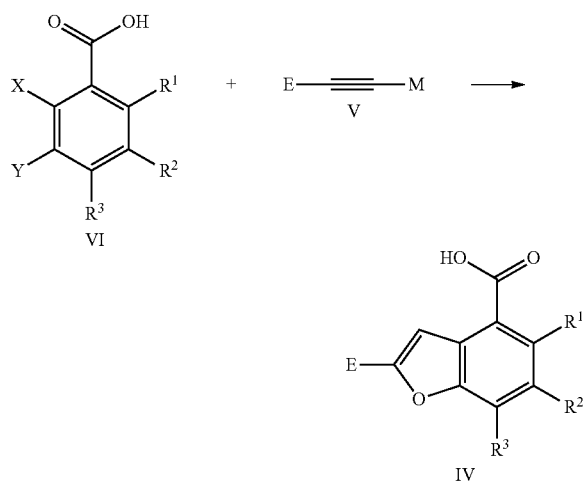

wherein X and Y are each independently selected from fluorine, chlorine, bromine, iodine, —OS(O)$_2$alkyl and —OS(O)$_2$aryl, preferably iodine and bromine;

$R^1$, $R^2$, $R^3$ are each identical or different, and are each independently selected from the group consisting of hydrogen atom, halogen, alkyl, haloalkyl, alkoxy, haloalkoxy, amino, nitro, hydroxyl, cyano, cycloalkyl, heterocyclyl, aryl, heteroaryl, —OR$^4$, —C(O)R$^4$, —C(O)OR$^4$, —OS(O)$_2$alkyl, and —OS(O)$_2$aryl, —S(O)$_m$R$^4$, —S(O)$_m$NR$^5$R$^6$ and —(CH$_2$)xR$^a$, wherein alkyl, haloalkyl, heterocyclyl, aryl and heteroaryl are each independently and optionally substituted by one or more substituents selected from the group consisting of alkyl, haloalkyl, halogen, amino, nitro, cyano, hydroxyl, alkoxy, haloalkoxy, hydroxyalkyl, cycloalkyl, heterocyclyl, aryl and heteroaryl;

E is selected from the group consisting of hydrogen atom, halogen, alkyl, haloalkyl, alkoxy, haloalkoxy, nitro, cyano, cycloalkyl, heterocyclyl, aryl, heteroaryl, —OR$^4$, —C(O)R$^4$, —C(O)OR$^4$, —OS(O)$_2$ alkyl, and —OS(O)$_2$ aryl, —S(O)$_m$R$^4$, —S(O)$_m$NR$^5$R$^6$ and —(CH$_2$)xR$^a$, wherein the alkyl, haloalkyl, heterocyclyl, aryl and heteroaryl are each independently and optionally substituted by any one or more substituents selected from the group consisting of alkyl, haloalkyl, halogen, amino, nitro, cyano, hydroxyl, alkoxy, haloalkoxy, hydroxyalkyl, cycloalkyl, heterocyclyl, aryl and heteroaryl;

R$^a$ is selected from the group consisting of halogen, cycloalkyl, heterocyclyl and —NR$^5$R$^6$, wherein the cycloalkyl and heterocyclyl are independently and optionally substituted by one or more substituents selected from the group consisting of alkyl, haloalkyl, halogen, amino, nitro, cyano, hydroxyl, alkoxy, haloalkoxy, hydroxyalkyl, cycloalkyl, heterocyclyl, aryl and heteroaryl;

R$^4$ is selected from the group consisting of hydrogen atom, alkyl, haloalkyl, alkoxy, hydroxyalkyl, hydroxyl, amino, cycloalkyl, heterocyclyl, aryl and heteroaryl;

R$^5$ and R$^6$ are each identical or different, and are each independently selected from the group consisting of hydrogen atom, alkyl, alkoxy, hydroxyalkyl, hydroxyl, amino, carboxylate, cycloalkyl, heterocyclyl, aryl and heteroaryl, wherein the alkyl, amino, cycloalkyl, heterocyclyl, aryl and heteroaryl are each independently and optionally substituted by one or more substituents selected from the group consisting of alkyl, halogen, hydroxyl, amino, carboxylate, nitro, cyano, alkoxy, hydroxyalkyl, cycloalkyl, heterocyclyl, aryl and heteroaryl;

M is selected from carboxyl, hydrogen and silicyl, preferably hydrogen;

m is 0, 1 or 2;

x is 0, 1, 2 or 3.

The present invention provides the method for preparing a compound represented by formula IV, wherein the reacting of the compound represented by formula VI with the compound represented by formula V is performed under the action of at least one metal catalyst and/or at least one alkaline substance.

The present invention provides the method for preparing a compound represented by formula IV, wherein the metal catalyst is selected from a metal palladium catalyst, a metal zinc catalyst, a metal copper catalyst and a metal nickel catalyst, preferably a metal copper catalyst, and more preferably a monovalent metal copper catalyst. Non-limiting examples of the metal catalysts described in the present invention include Pd$_2$(dba)$_3$, Pd(dba)$_2$, Pd(PPh$_3$)$_4$, (Ph$_3$P)$_2$PdCl$_2$, Pd(OAc)$_2$, Pd(tfa)$_2$, Pd(Piv)$_2$, Pd(OTf)$_2$, CuCl, Cu$_2$O, ZnCl$_2$, preferably CuI.

The present invention provides the method for preparing a compound represented by formula IV, wherein the alkaline substance is selected from the group consisting of KHCO$_3$, NaHCO$_3$, Na$_2$CO$_3$, Ba(OH)$_2$, K$_3$PO$_4$, Cs$_2$CO$_3$, K$_2$CO$_3$, KF, CsF, KCN, NaCN, NaOH, KOH, Et$_3$N, DIPEA, DABCO, NaOMe, NaOEt, $^t$BuOK, $^t$BuONa, NaH, DBU, TMG, LHMDS, NaHMDS, n-BuLi, sodium tert-pentoxide, diethylamine and dicyclohexylamine, preferably $^t$BuOK and $^t$BuONa.

The present invention provides the method for preparing a compound represented by formula IV, wherein the reaction solvent is one or more selected from the group consisting of ethyl acetate, dimethylformamide, 1-methyl-2-pyrrolidone, tetrahydrofuran, methyltetrahydrofuran, dioxane, toluene, xylene, dimethylsulfoxide, diethyl ether, isopropyl ether, methyl tert-butyl ether, acetonitrile, propionitrile, isopropanol, propanol, ethanol, methanol and water.

The present invention provides the method for preparing a compound represented by formula IV, wherein the reaction is carried out under the protection of an inert gas selected from nitrogen, argon and helium, preferably argon.

The present invention provides a method of a compound represented by formula VIa reacting with a compound represented by formula Va to give a compound represented by formula IVa,

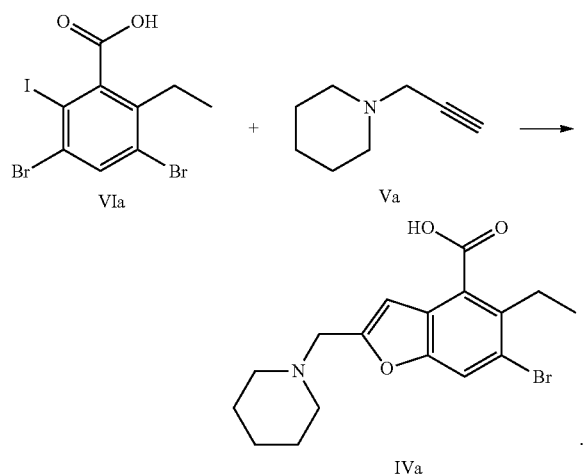

The present invention also provides a method for preparing a compound represented by formula VIa, which comprises the step of giving the compound represented by formula VIa by using a compound represented by formula VIIa under the action of a brominating reagent and at least one acid,

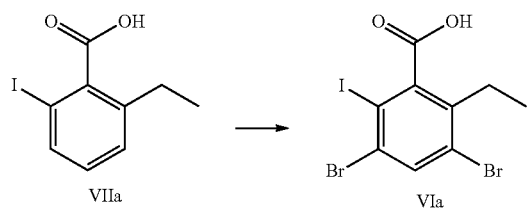

The present invention provides the method for preparing a compound represented by formula IVa, wherein the brominating reagent is selected from the group consisting of HBr, $Br_2$, NBS, DBDMH, HOBr, AcOBr, $CF_3COOBr$, $NH_4Br$, TBBDA, PBBS and tribromoisocyanurate, preferably NBS or DBDMH.

The present invention provides the method for preparing a compound represented by formula IVa, wherein the acid is selected from the group consisting of $AlCl_3$, $SbCl_5$, $FeCl_3$, $FeBr_3$, $SnCl_4$, $TiCl_4$, $ZnCl_2$, $BF_3$, acetic acid, sulfuric acid, hydrochloric acid and trifluoroacetic acid, preferably sulfuric acid or trifluoroacetic acid.

The present invention provides the method for preparing a compound represented by formula IVa, optionally comprises the method for preparing the compound represented by formula VIa according to the present invention.

The present invention provides the method for preparing a compound represented by formula IV, wherein the reaction is carried out under the protection of an inert gas selected from nitrogen, argon and helium, preferably argon.

The present invention also provides a method for preparing a compound represented by formula VIIa, wherein the compound represented by formula VIIa is prepared by reacting of the compound represented by formula VIIIa under the action of at least one or more palladium catalysts selected from the group consisting of $Pd_2(dba)_3$, $Pd(dba)_2$, $Pd(OAc)_2$, $Pd(tfa)_2$, $Pd(Piv)_2$, $Pd(OTf)_2$, $Pd(PPh_3)_4$, $PdCl_2$, $Pd(PPh_3)_2Cl_2$ and $Pd(dppf)Cl_2$, and one or more iodine reagents selected from the group consisting of NIS, $I(Py)_2BF_4$, IOAC, KI, $KIO_3$, NaI and IBr, wherein the palladium catalyst is preferably $Pd(OAc)_2$, and the iodine reagent is preferably NIS.

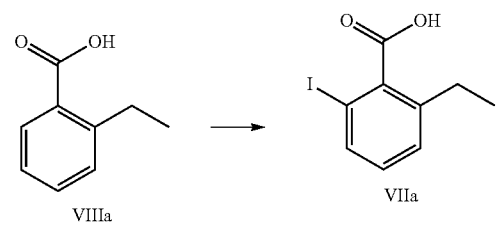

The present invention provides the method for preparing a compound represented by formula VIIa, wherein the reaction is carried out under the protection of an inert gas selected from nitrogen, argon and helium, preferably argon.

The present invention provides the method for preparing a compound represented by formula VIIa, wherein the amount of catalyst used is 0.01%-20%, preferably 0.1%-10%, and most preferably 1%-5% of the compound of formula VIIIa.

The present invention provides the method for preparing a compound represented by formula VIIa, wherein the reaction solvent is not specifically limited, and exemplary solvents may be selected from the group consisting of N,N-dimethylformamide, N,N-dimethylacetamide, dichloromethane, ethanol, methanol, dimethylsulfoxide, acetonitrile, acetone, chloroform.

The method for preparing a compound represented by formula VIa provided by the present invention optionally includes a step of preparing a compound represented by formula VIIa provided by the present invention.

The present invention also provides a method for preparing a compound represented by formula IIIa, wherein the compound represented by formula IIIa is prepared by reacting of the compound represented by formula IVa with tetrahydro-2H-pyran-4-amine,

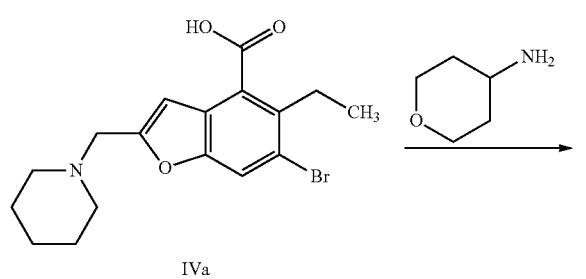

IVa

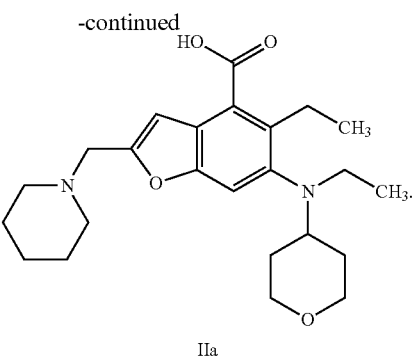

IIa

The method for preparing a compound represented by formula IIa provided by the present invention optionally comprises the compound represented by formula IIIa, the compound represented by formula IVa, the compound represented by formula VIa, and the compound represented by formula VIIa provided by the present invention The present invention also provides a method for preparing a compound represented by formula Ia, which comprises the step of compound represented by formula IIa reacting with 3-(aminomethyl)-4,6-dimethylpyridine-2(1H)-one hydrochloride to give formula Ia, which further comprises the method for preparing the compound represented by formula IIa according to the claims and the present invention,

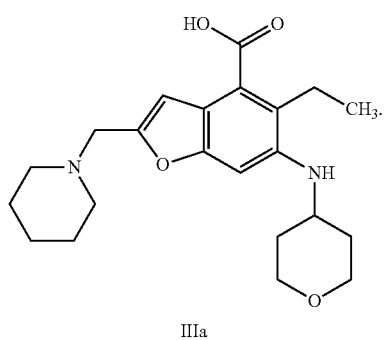

IIIa

The method for preparing a compound represented by formula IIIa provided by the present invention can be carried out under the action of DPE-Phos, sodium tert-butoxide and palladium catalyst.

The method for preparing a compound represented by formula IIIa provided by the present invention optionally comprises the method for preparing the compound represented by formula IVa, the compound represented by formula VIa, and the compound represented by formula VIIa provided by the present invention.

The present invention also provides a method for preparing a compound represented by formula IIa, wherein the compound represented by formula IIIa undergoes N-ethylation to give a compound represented by formula IIa, IIIa IIa The method for preparing a compound represented by formula Ia provided by the present invention, optionally further comprises the method for preparing a compound represented by formula IIIa provided by the present invention.

The method for preparing a compound represented by formula Ia provided by the present invention, optionally further comprises the method for preparing a compound represented by formula IVa provided by the present invention.

The present invention also provides a compound represented by formula IV,

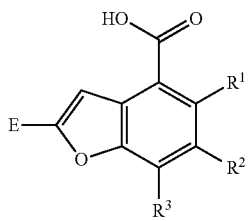

wherein E, $R^1$, $R^2$, $R^3$ are as defined above.

The present invention also provides a compound represented by formula VI,

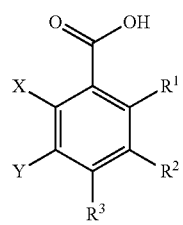

wherein X, Y, $R^1$, $R^2$, $R^3$ are as defined above.

The present invention also provides a compound represented by formula VIa:

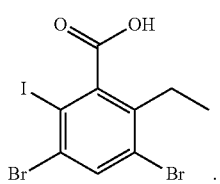

The present invention also provides a compound represented by formula IVa:

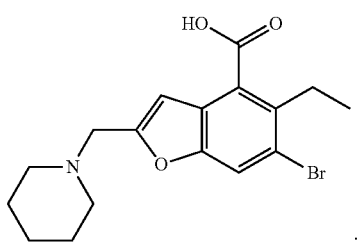

The present invention also provides a compound represented by formula IIIa:

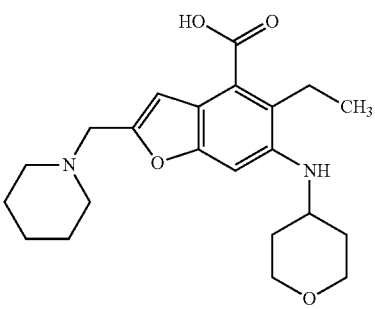

The method for producing the compound represented by formula IIa using the compound represented by formula IIIa provided by the present invention can specifically refer to the similar preparation method disclosed in Example 1 of PCT application WO2017084494A

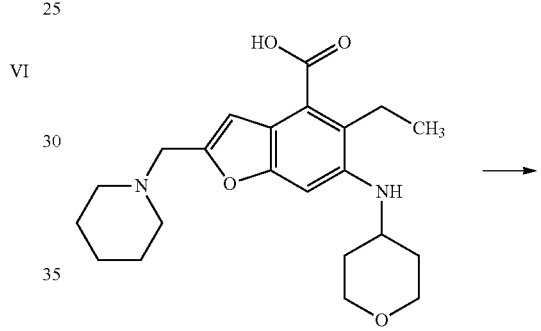

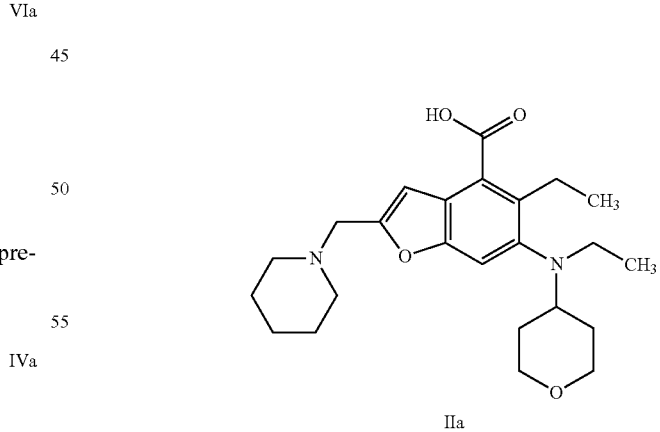

The method for producing the compound represented by formula Ia using the compound represented by formula IIa provided by the present invention can specifically refer to the methods for preparing amides disclosed in PCT applications WO2017084494A, WO2012142513, WO2013039988, WO2015-141616 and WO2011140325

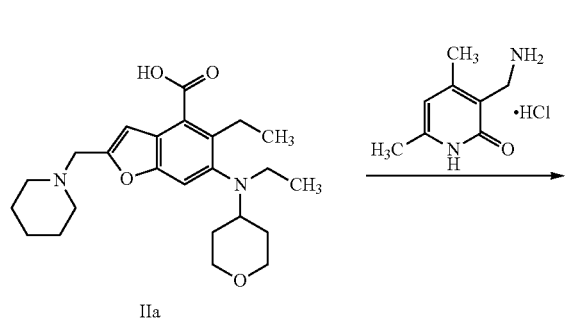
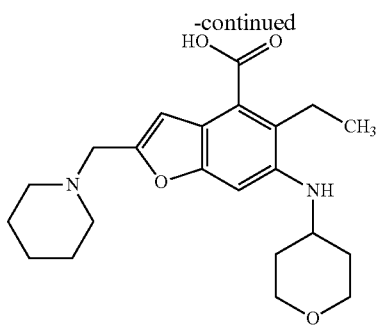

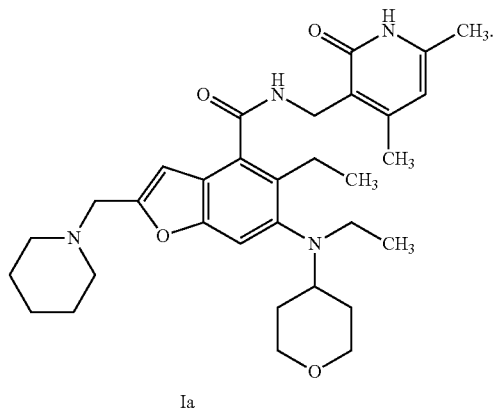

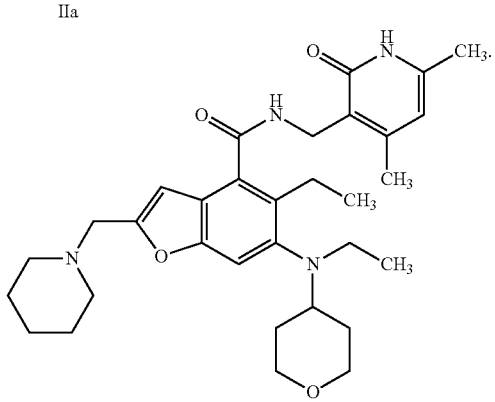

The compound represented by the formula Ia provided by the present invention can be specifically prepared using the following route, and the reaction conditions can be selected from the conditions as defined in each of the specific steps described above

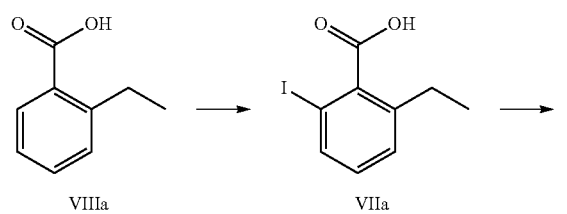

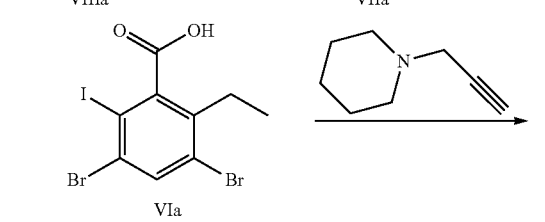

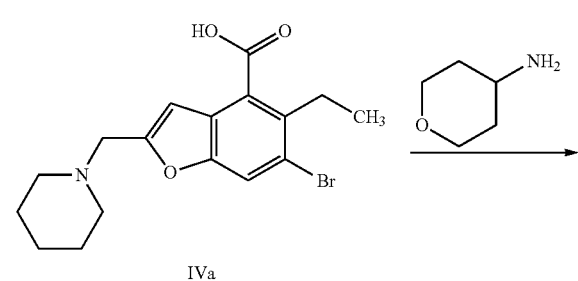

DETAILED DESCRIPTION OF THE INVENTION

Unless stated to the contrary, terms used in the specification and claims herein have the following meanings.

The term 'alkyl' refers to a saturated aliphatic hydrocarbon group, which is a linear or branched chain group containing 1 to 20 carbon atoms, preferably an alkyl containing 1 to 12 carbon atoms, and more preferably an alkyl containing 1 to 6 carbons carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3- ethylhexyl, 2,2-diethylpentyl, n-decyl, 3,3-diethylhexyl, 2,2-diethylhexyl, and various branched chain isomers thereof. More preferred are lower alkyl containing 1 to 6 carbon atoms, non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl may be substituted or unsubstituted. When substituted, the substituent may be substituted at any available joinpoint. The substituent is preferably one or more substituents independently selected from the following group consisting of alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkyloxy, heterocycloalkyloxy, cycloalkylthio, heterocycloalkylthio, oxo, carboxyl or carboxylate.

The term 'alkylene' refers to the further substitution of a hydrogen atom of an alkyl, for example: 'methylene' refers to —CH$_2$—, 'ethylidene' refers to —(CH$_2$)$_2$—, 'propylidene' refers to —(CH$_2$)$_3$—, 'butylidene' refers to —(CH$_2$)$_4$—, and the like.

The term 'alkenyl' refers to an alkyl, as defined above, consisting of at least two carbon atoms and at least one carbon-carbon double bond, such as vinyl, 1-propenyl, 2-propenyl, 1-, 2-, or 3-butenyl and the like. Alkenyl can be substituted or unsubstituted. When substituted, the substituent is preferably one or more substituents independently selected from the following group consisting of alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkyloxy, heterocycloalkyloxy, cycloalkylthio, heterocycloalkylthio.

The term 'spirocycloalkyl' refers to a polycyclic group of 5- to 20-membered, preferably 6- to 14-membered, and more preferably 7- to 10-membered monocycles that shares one carbon atom (called a spiro atom), which may contain one or more double bonds, but none of the rings have a fully conjugated π-electronic system. According to the number of shared spiro atoms among the rings, the spirocycloalkyl consists of monospirocycloalkyl, bisspirocycloalkyl or polyspirocycloalkyl, preferably monospirocycloalkyl and bisspirocycloalkyl, more preferably 4-membered/4-membered, 4-membered/5-membered, 4-membered/6-membered, 5-membered/5-membered, or 5-membered/6-membered monospirocycloalkyl. Non-limiting examples of spirocycloalkyl include:

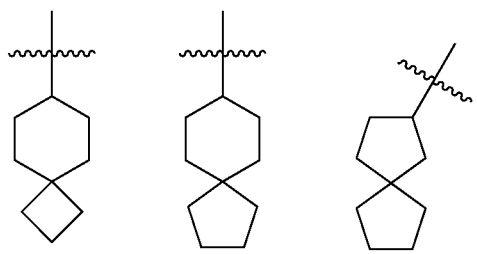

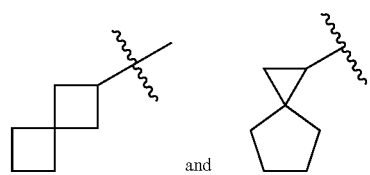

and

The term 'condensed cycloalkyl' refers to a 5- to 20-membered, preferably 6- to 14-membered, and more preferably 7- to 10-membered all-carbon polycyclic group in which each ring in the system shares a pair of adjacent carbon atoms with other rings in the system, wherein one or more rings may contain one or more double bonds, but none of the rings have a fully conjugated π-electronic system. According to the number of rings, the condensed cycloalkyl consists of bicyclic, tricyclic, tetracyclic or polycyclic condensed cycloalkyl, preferably bicyclic or tricyclic, more preferably 5-membered/5-membered or 5-membered/6-membered bicyclic alkyl. Non-limiting examples of condensed cycloalkyl include:

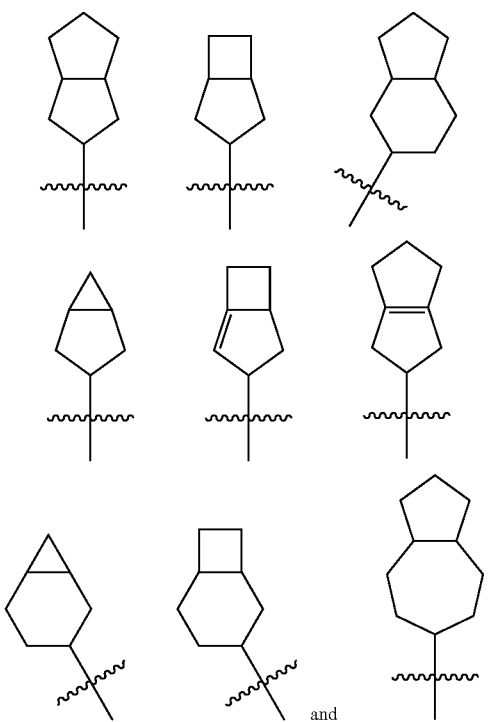

and

The term 'bridged cycloalkyl' refers to a 5- to 20-membered, preferably 6- to 14-membered, and more preferably 7- to 10-membered all-carbon polycyclic group in which any two rings share two carbon atoms that are not directly connected, which may contain one or more double bonds, but none of the rings have a fully conjugated π-electronic system. According to the number of rings, the bridged cycloalkyl consists of bicyclic, tricyclic, tetracyclic or polycyclic bridged cycloalkyl, preferably bicyclic, tricyclic or tetracyclic, and more preferably bicyclic or tricyclic bridged cycloalkyl. Non-limiting examples of bridged cycloalkyl include:

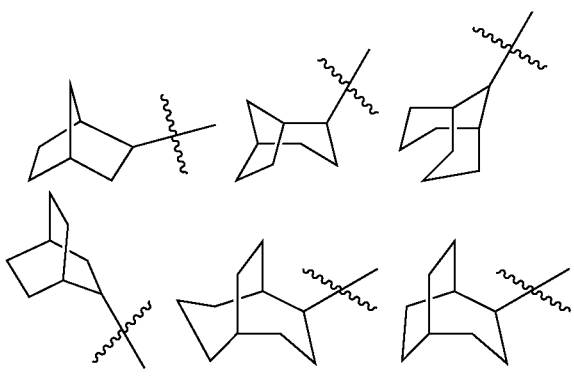

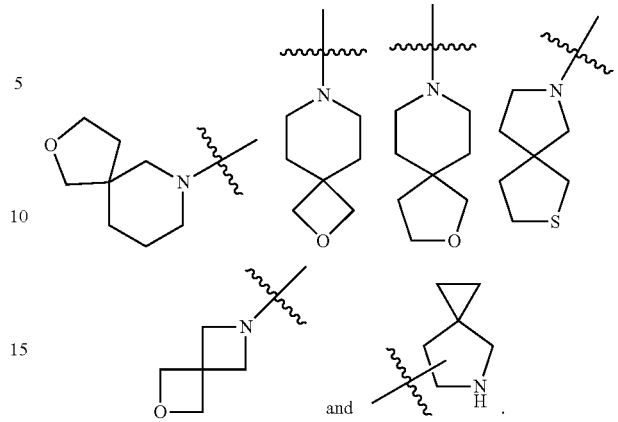

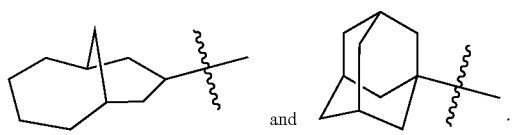

The cycloalkyl ring may be condensed to aryl, heteroaryl or heterocycloalkyl rings, wherein the ring connected to the parent structure is cycloalkyl, and non-limiting examples include indanyl, tetrahydronaphthyl, benzocycloheptyl and the like. Cycloalkyl may be optionally substituted or unsubstituted, and when substituted, the substituent is preferably one or more substituents independently selected from the following group consisting of alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkyloxy, heterocycloalkyloxy, cycloalkylthio, heterocycloalkylthio, oxo, carboxyl and carboxylate.

The term 'cycloalkyl' refers to a saturated or partially unsaturated monocyclic or polycyclic hydrocarbon substituent. The cycloalkyl ring contains 3 to 20 carbon atoms, preferably 3 to 12 carbon atoms, and more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like; polycyclic cycloalkyl includes spiro, condensed and bridged cycloalkyl.

The term 'spiroheterocyclyl' refers to a polycyclic heterocyclyl of 5- to 20-membered, preferably 6- to 14-membered, and more preferably 7- to 10-membered monocycles which shares one atom (called spiro atom), wherein one or more ring atoms are heteroatoms selected from nitrogen, oxygen, or S(O)$_m$ (wherein m represents an integer from 0 to 2), and the remaining ring atoms are carbon. It can contain one or more double bonds, but none of the rings have a fully conjugated a-electronic system. According to the number of common spiro atoms among the rings, the spiroheterocyclyl consists of monospiroheterocyclyl, bisspiroheterocyclyl or polyspiroheterocyclyl, preferably monospiroheterocyclyl and bisspiroheterocyclyl, more preferably 4-membered/4-membered, 4-membered/5-membered, 4-membered/6-membered, 5-membered/5-membered, or 5-membered/6-membered monospirocycloalkyl. Non-limiting examples of spiroheterocyclyl include:

The term 'condensed heterocyclyl' refers to a 5- to 20-membered, preferably 6- to 14-membered, and more preferably 7- to 10-membered polycyclic heterocyclyl in which each ring in the system shares a pair of adjacent atoms with other rings in the system. One or more rings may contain one or more double bonds, but none of the rings have a fully conjugated π-electronic system, wherein one or more ring atoms are heteroatoms selected from nitrogen, oxygen, or S(O)$_m$ (wherein m is an integer from 0 to 2), and the remaining ring atoms are carbon. According to the number of rings, the condensed heterocyclyl consists of bicyclic, tricyclic, tetracyclic or polycyclic condensed heterocyclyl preferably bicyclic or tricyclic, more 5-membered/5-membered, or 5-membered/6-membered bicyclic condensed heterocyclyl. Non-limiting examples of condensed heterocyclyl include:

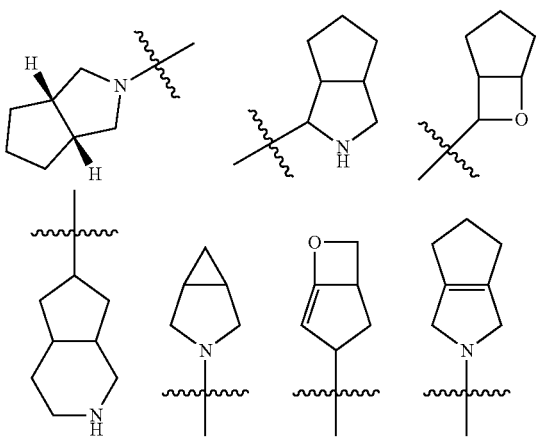

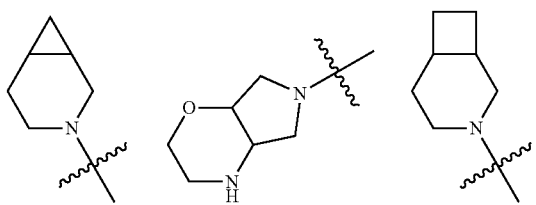

-continued

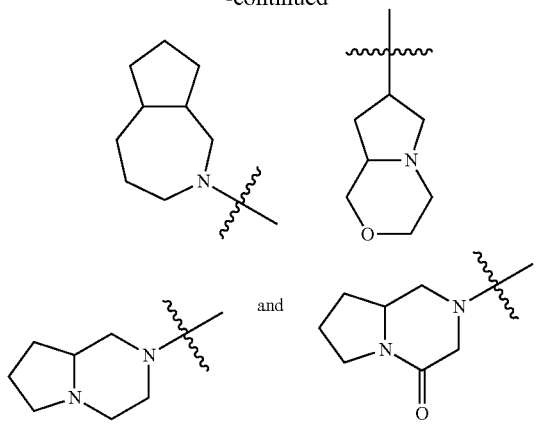

The term 'bridged heterocyclyl' refers to a 5- to 14-membered, preferably 6- to 14-membered, and more preferably 7- to 10-membered polycyclic heterocyclyl in which any two rings share two atoms that are not directly connected, which may contain one or more double bonds, but none of the rings have a fully conjugated π-electronic system, wherein one or more ring atoms are heteroatoms selected from nitrogen, oxygen, or S(O)$_m$ (wherein m is an integer of 0 to 2), and the remaining ring atoms are carbon. According to the number of rings, the bridged heterocyclyl consists of bicyclic, tricyclic, tetracyclic or polycyclic bridged heterocyclyl, preferably bicyclic, tricyclic or tetracyclic, and more preferably bicyclic or tricyclic. Non-limiting examples of bridged heterocyclyls include:

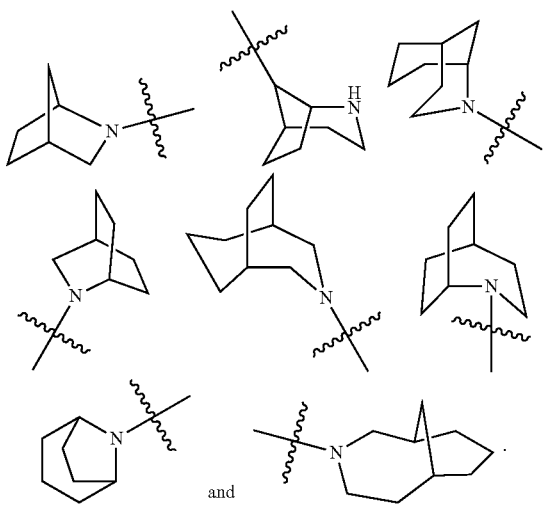

The heterocyclyl ring may be condensed to aryl, heteroaryl or cycloalkyl ring, wherein the ring connected to the parent structure is heterocyclyl, and non-limiting examples include:

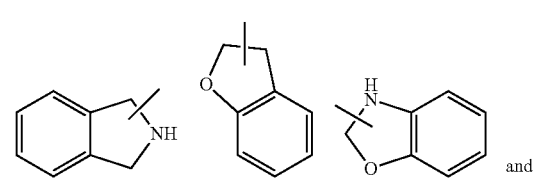

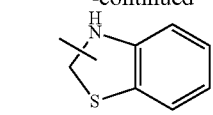

The heterocyclyl may be optionally substituted or unsubstituted, when substituted, the substituent is preferably one or more substituents independently selected from the following group consisting of alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkyloxy, heterocycloalkyloxy, cycloalkylthio, heterocycloalkylthio, oxo, carboxyl and carboxylate.

The term 'heterocyclyl' refers to a saturated or partially unsaturated monocyclic or polycyclic hydrocarbon substituent that contains 3 to 20 ring atoms, wherein one or more ring atoms are heteroatoms selected from nitrogen, oxygen, or S(O)$_m$ (wherein m is an integer of 0 to 2), but does not include a ring portion of —O—O—, —O—S—, or —S—S—, and the remaining ring atoms are carbon. It preferably contains 3 to 12 ring atoms, of which 1 to 4 are heteroatoms; most preferably contains 3 to 8 ring atoms, of which 1 to 3 are heteroatoms; and most preferably contains 3 to 6 ring atoms, of which 1 to 2 are heteroatoms. Non-limiting examples of monocyclic heterocyclyl include pyrrolidinyl, imidazolidinyl, tetrahydrofuryl, tetrahydrothienyl, dihydroimidazolyl, dihydrofuryl, dihydropyrazolyl, dihydropyrrolyl, piperidyl, piperazinyl, morpholinyl, thiomorpholinyl, homopiperazinyl, pyranyl, etc., preferably piperidinyl, pyrrolidinyl, pyranyl, morpholinyl or

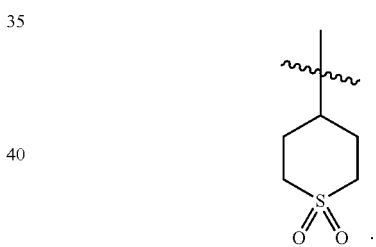

Polycyclic heterocyclyls include spiro, condensed and bridged heterocyclyl.

The term 'aryl' refers to a 6- to 14-membered, preferably 6- to 10-members all-carbon monocyclic or condensed polycyclic (ie, rings that share pairs of adjacent carbon atoms) group having a fully conjugated π-electronic system, such as benzene and naphthyl, more preferably phenyl. The aryl ring may be condensed to heteroaryl, heterocyclyl or cycloalkyl ring, wherein the ring connected to the parent structure is an aryl ring, and non-limiting examples thereof include:

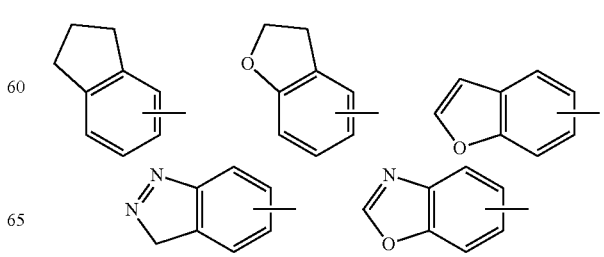

-continued

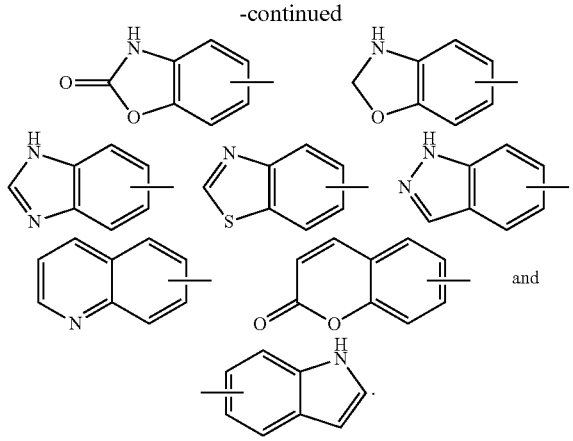

The aryl may be substituted or unsubstituted. When substituted, the substituent is preferably one or more substituents independently selected from the following group consisting of alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkyloxy, heterocycloalkyloxy, cycloalkylthio, heterocycloalkylthio, carboxyl and carboxylate.

The term 'heteroaryl' refers to a heteroaromatic system containing 1 to 4 heteroatoms, 5 to 14 ring atoms, wherein the heteroatoms are selected from oxygen, sulfur and nitrogen. Heteroaryl is preferably 5- to 10-members, containing 1 to 3 heteroatoms; more preferably 5- or 6-members, containing 1 to 2 heteroatoms; preferably, for example, imidazolyl, furyl, thienyl, thiazolyl, pyrazolyl, oxazolyl, pyrrolyl, tetrazolyl, pyridyl, pyrimidinyl, thiadiazole, pyrazinyl, etc., preferably imidazolyl, tetrazolyl, thienyl, pyrazolyl or pyrimidyl, thiazolyl ; more preferably pyrazolyl or thiazolyl. The heteroaryl ring may be condensed to aryl, heterocyclyl or cycloalkyl ring, wherein the ring connected to the parent structure is heteroaryl ring, and non-limiting examples include:

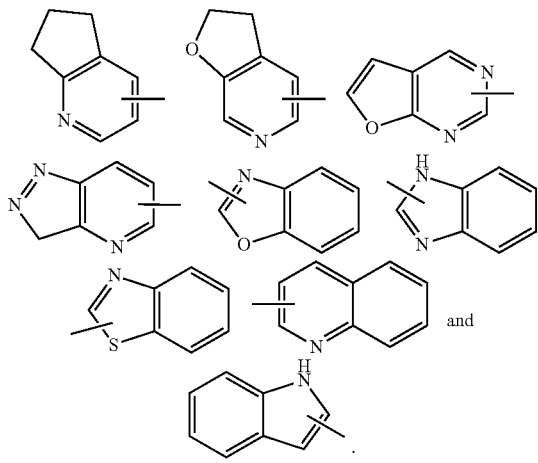

Heteroaryl may be optionally substituted or unsubstituted. When substituted, the substituent is preferably one or more substituents independently selected from the following group consisting of alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkyloxy, heterocycloalkyloxy, cycloalkylthio, heterocycloalkylthio, carboxyl and carboxylate.

The term 'alkoxy' refers to —O-(alkyl) and —O-(unsubstituted cycloalkyl), wherein the alkyl is as defined above. Non-limiting examples of the alkoxy include: methoxy, ethoxy, propoxy, butoxy, cyclopropoxy, cyclobutoxy, cyclopentyloxy, cyclohexyloxy. The alkoxy may be optionally substituted or unsubstituted. When substituted, the substituent is preferably one or more substituents independently selected from the following group consisting of alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkyloxy, heterocycloalkyloxy, cycloalkylthio, heterocycloalkylthio, carboxyl and carboxylate.

The term 'haloalkyl' refers to an alkyl substituted with one or more halogens, wherein the alkyl is as defined above.

The term 'haloalkoxy' refers to an alkoxy group substituted with one or more halogens, where alkoxy is as defined above.

The term 'hydroxyalkyl' refers to an alkyl substituted with hydroxy, wherein the alkyl is as defined above.

The term 'hydroxyl' refers to —OH.

The term 'halogen' refers to fluorine, chlorine, bromine or iodine.

The term 'amino' refers to —NH$_2$.

The term 'cyano' refers to —CN.

The term 'nitro' refers to —NO$_2$.

The term 'oxo' refers to =O.

The term 'carbonyl' refers to C=O.

The term 'carboxy' refers to —C(O)OH.

The term 'isocyanate' refers to —NCO.

The term 'oxime' refers to =N—OH.

The term 'carboxylate' refers to —C(O)O(alkyl) or —C(O)O(cycloalkyl), wherein the alkyl and the cycloalkyl are as defined above.

'Optional' or 'optionally' means that the event or environment described subsequently may, but need not, occur, and the description includes situations where the event or environment occurs or does not occur. For example, 'optionally heterocyclyl substituted with alkyl' means that the alkyl may but need not exist, and this description includes a case where the heterocyclyl is substituted with alkyl and a case where the heterocyclic group is not substituted with alkyl.

'Substituted' refers to one or more hydrogen atoms in a group, preferably up to 5 and more preferably 1 to 3 hydrogen atoms are each independently substituted with a corresponding number of substituents. It goes without saying that the substituents are only in their possible chemical positions, and those skilled in the art can determine (by experiment or theory) possible or impossible substitutions without undue effort. For example, an amino or a hydroxyl having free hydrogen may be unstable when combined with a carbon atom having an unsaturated (eg, olefinic) bond.

Unless stated to the contrary, the English abbreviations used in specification and claims herein have the following meanings

| | | | |
|---|---|---|---|
| DIPEA | diisopropylethylamine | DABCO | 1,4-diazabicyclo[2.2.2]octane |
| tBuOK | potassium tert-butoxide | tBuONa | sodium tert-butoxide |
| LHMDS | lithium bis(trimethylsilyl)amide | DBU | 1,8-diazabicyclo(5.4.0)undec-7-ene |
| Py | pyridine | NaHMDS | sodium bis(trimethylsilyl)amide |
| TMG | N,N',N',N'-tetramethyl guanidine | dppf | 1,1'-bis(diphenylphosphino)ferrocene |
| APTDC | Ammonium pyrrolidine dithiocarbamate | n-BuLi | n-butyllithium |
| NBS | N-bromosuccinimide | DBDMH | 1,3-Dibromo-5,5-dimethylhydantoin |
| HOBr | hypobromous acid | TBBDA | N,N,N',N'-tetrabromobenzene-1,3-disulfonamide |
| $SbCl_5$ | antimony pentachloride | PBBS | poly(N-bromobenzene-1,3-disulfonamide) |
| $TiCl_4$ | titanium tetrachloride | NIS | N-Iodosuccinimide |
| $Pd_2(dba)_3$ | Tris(dibenzylideneacetone)dipalladium | $Pd(dba)_2$ | bis(dibenzylideneacetone)palladium |
| $Pd(OAc)_2$ | palladium acetate | $Pd(tfa)_2$ | trifluoroacetyl palladium |
| $Pd(Piv)_2$ | trimethyl palladium acetate | $Pd(OTf)_2$ | trifluoromethanesulfonyl palladium |
| $Pd(PPh_3)_4$ | tetrakis(triphenylphosphine)palladium | $PdCl_2$ | palladium chloride |
| $Pd(PPh_3)_2Cl_2$ | bis(triphenylphosphine)palladium(II) dichloride | $Pd(dppf)Cl_2$ | [1,1'-Bis(diphenylphosphino)ferrocene]dichloropalladium(II) |
| $Pd(OAc)_2$ | palladium acetate | IBr | iodine bromide |
| $I(Py)_2BF_4$ | bis(pyridine)iodonium Tetrafluoroborate | DPE-Phos | bis(2-diphenylphosphinophenyl)ether |

DETAILED DESCRIPTION OF THE PREFERRED EMBODIMENT

The present invention is illustrated in detail below with reference to specific examples, so that those skilled in the art can fully understand the present invention that the following examples are only used to illustrate the technical solution of the present invention, and not intended to limit the present invention in any way.

The structure of the compound is determined by nuclear magnetic resonance (NMR) or mass spectrometry (MS). NMR was measured using a Bruker AVANCE-400 nuclear magnetic analyzer. The measurement solvents were deuterated dimethyl sulfoxide (DMSO-d6), deuterated chloroform (CDCl3) and deuterated methanol (CD3OD). The internal standard was tetramethylsilane (TMS), and the chemical shift is given in units of $10^{-6}$ (ppm).

MS was measured using a FINNIGAN LCQAd (ESI) mass spectrometer (manufacturer: Thermo, model: Finnigan LCQ advantage MAX).

HPLC was measured using a WATER e2695-2489 high performance liquid chromatograph.

The known starting materials of the present invention can be synthesized by or according to methods known in the art, or can be purchased from companies such as BEPHARM.

Embodiment 1

Step 1: 2-ethyl-6-iodobenzoic acid

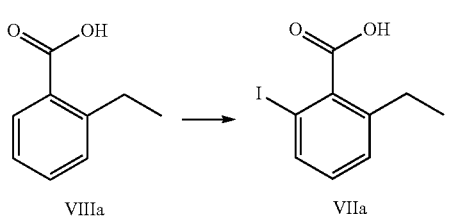

VIIIa (100 g, 667 mmol) was dissolved in 1000 mL of N,N-dimethylformamide, stirred to dissolve, NIS (165 g, 733 mmol) and Pd(OAc)2 (3 g, 13.4 mmol) were added in order, the mixture was degassed twice with argon. The reaction mixture was stirred at 100° C. and monitored by thin layer chromatography. The reaction was stopped once the complete conversion of the material VIIIa.

Post-treatment: the reaction solution was poured into 2 L of water, extracted with ethyl acetate for three times, and the organic phases were combined and concentrated to remove most of the ethyl acetate. Subsequently, extract was washed with a saturated sodium thiosulfate solution and a saturated sodium chloride solution successively, then the organic phases were dried over anhydrous sodium sulfate and filtered. The filtrate was concentrated under reduced pressure to obtain 184 g of crude product, m/z [M–H]$^-$=275.1, $^1$H NMR (400 MHz, CHLOROFORM-d) □ ppm: 11.85 (br. s., 1H), 7.72 (d, 1H), 7.28 (d, 1H), 7.07-7.14 (m, 1H), 2.78 (q, 2H), 1.29 (t, 3H), and the product was subjected to the next reaction without purification.

Step 2: 3,5-dibromo-2-ethyl-6-iodobenzoic acid

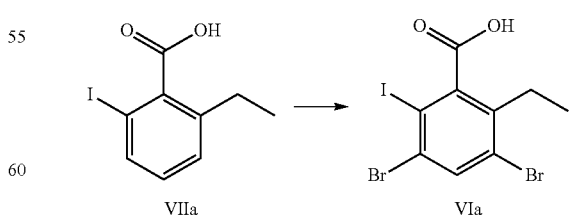

VIIa (27.6 g, 83 mmol) was dissolved in 138 mL of concentrated sulfuric acid (5 mL/g), the temperature was lowered to 0-5° C., a solution of N-bromosuccinimide (19.6 g, 110 mmol) in trifluoroacetic acid was added dropwise.

The above-mentioned trifluoroacetic acid solution of N-bromosuccinimide was slowly added to the reaction solution. After the addition, the temperature was naturally raised to room temperature and reaction was conducted for a period of time, then the temperature was continuously rise to 40° C., and a solution of N-bromosuccinimide (14.2 g, 80 mmol) in trifluoroacetic acid was added dropwise. The reaction was terminated after detecting VIIa<2%.

Post-treatment: the reaction solution was poured into 4 times the volume of ice water, and the solid was precipitated and filtered. The solid was dissolved with ethyl acetate, dried over anhydrous sodium sulfate, and spin-dried to obtain a crude product. The crude product was recrystallized with ethyl acetate, then dried in vacuo to obtain 29.5 g of white solid. The product has a yield of 82% and a purity of 95.0%. m/z [M−H]−=432.8

Step 3: 6-bromo-5-ethyl-2-(piperidin-1-ylmethyl) benzofuran-4-carboxylic acid

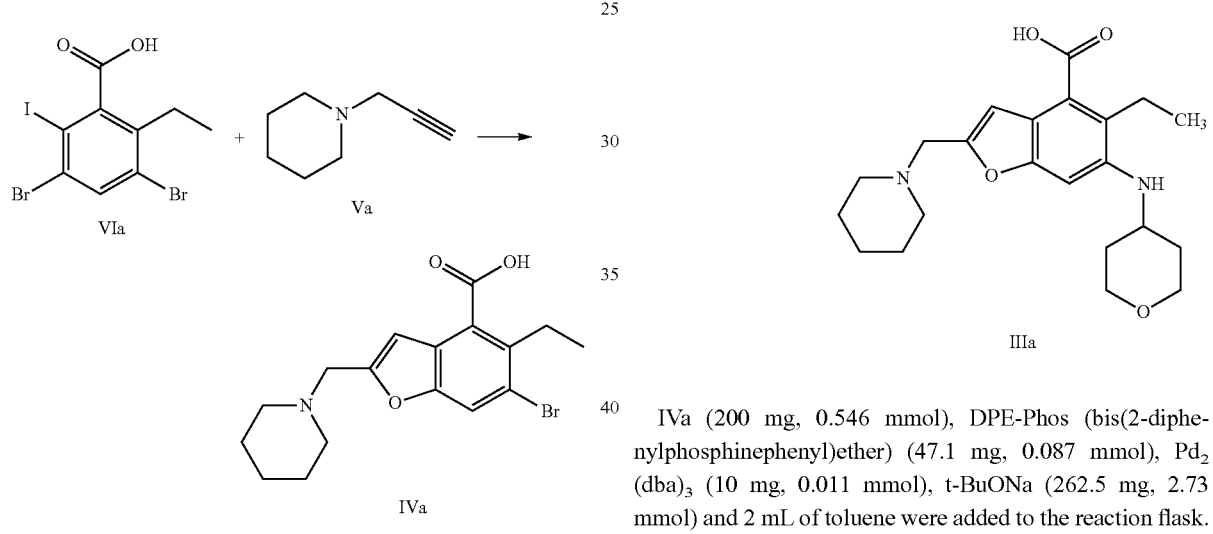

VIa (100 g, 230.4 mmol), cesium carbonate (187.6 g, 576 mmol), cuprous iodide (13.16 g, 69.12 mmol) and deionized water (16.6 g, 921.6 mmol) were dissolved in 800 mL of DMSO, Va (34.04 g, 276.5 mmol) was added, to the mixture was degassed three times with argon and the reaction mixture was heated to 110° C. The reaction was stirred for 5 hours and monitored by thin layer chromatography. The reaction was stopped once the disappearance of the starting material VIa.

Post-treatment: the reaction solution was filtered while it was hot, the filter cake was rinsed with a small amount of DMSO, and the filtrate was slowly poured into sodium chloride solution. The pH was adjusted to 5.5 with HCl solution in an ice bath, and solids were precipitated. After continuous stirring, filtration and vacuum drying, 48.8 g of the title product (off-white solid) with 97.3% of purity was recrystallized using isopropanol. m/z [M, M+2]=366, 368

Step 4: 5-ethyl-2-(piperidin-1-ylmethyl)-6-((tetrahydro-2H-pyran-4-yl)amino) benzofuran-4-carboxylic acid

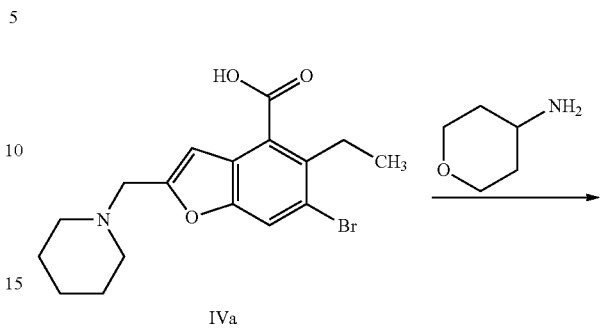

IVa (200 mg, 0.546 mmol), DPE-Phos (bis(2-diphenylphosphinephenyl)ether) (47.1 mg, 0.087 mmol), Pd$_2$(dba)$_3$ (10 mg, 0.011 mmol), t-BuONa (262.5 mg, 2.73 mmol) and 2 mL of toluene were added to the reaction flask. Tetrahydro-2H-pyran-4-amine (110.4 mg, 1.09 mmol) was added, the mixture was degassed three times with argon, and the reaction mixture was heated to 105-108° C. under oil bath. The reaction was stirred and monitored by thin layer chromatography. The reaction was stopped once the disappearance of the starting material IVa.

Post-treatment: the reaction solution was cooled to room temperature and poured into 10 mL of water. Adjusting pH to 7-8 with dilute hydrochloric acid, the aqueous phase was separated, and the pH of the aqueous phase was adjusted to about 6, which was near the isoelectric point, with dilute hydrochloric acid. Mixed solution of dichloromethane and methanol was used for extraction for three times, organic phases was combined, and dried over anhydrous sodium sulfate. After filtering and concentrating the filtrate under reduced pressure, column chromatography was carried out using eluent (dichloromethane:methanol=20:1) to obtain 120 mg of product IIIa (brown solid). m/z [M+H]+=387.4

Step 5: 5-ethyl-6-(ethyl(tetrahydro-2H-pyran-4-yl)amino)-2-(piperidin-1-ylmethyl)benzofuran-4-carboxylic acid

Step 6: N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide

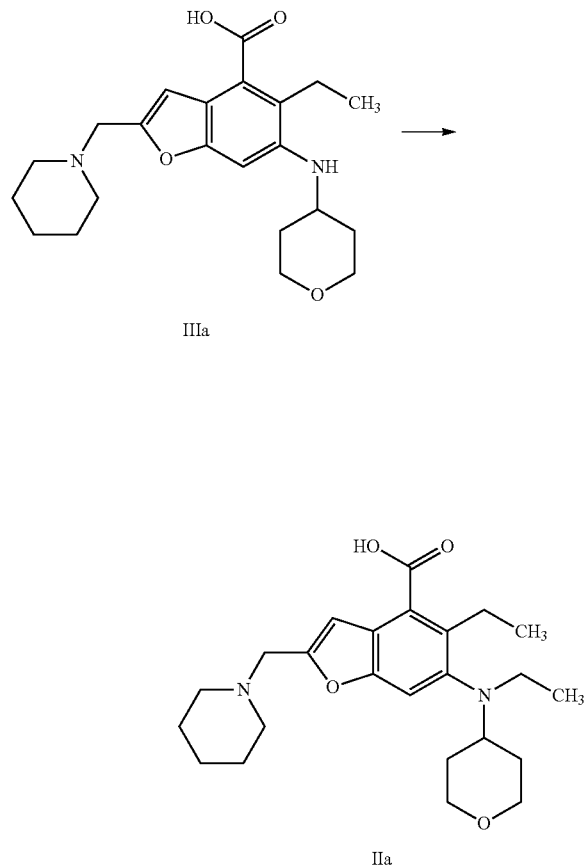

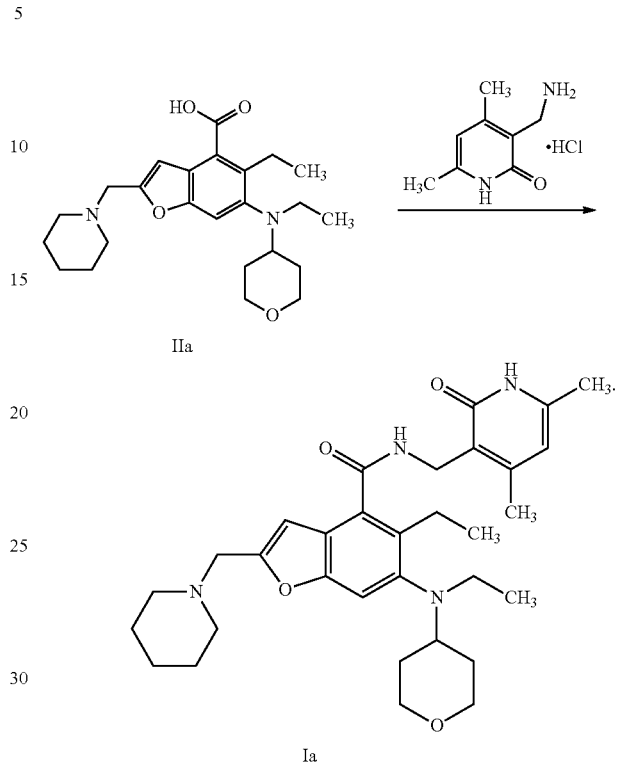

Material IIIa (120 mg, 0.31 mmol) was placed in a 25 mL three-necked flask, 3 mL of DCM was added. Acetaldehyde (69 mg, 1.55 mmol) and acetic acid (94 mg, 1.55 mmol) was added into the flask under ice bath, and the reaction was stirred for 0.5 hours. Sodium triacetoxyborohydride (198 mg, 0.93 mmol) was added in portions under ice bath, and the reaction was warmed to room temperature. The reaction is carried our while stirring, and terminated once the disappearance of the material IIIa was detected by thin layer chromatography.

Post-treatment: 50 mL of saturated sodium chloride solution was added to the reaction solution, and stirred for 0.5 hours. The layers were separated, and the organic phase was washed with a saturated sodium chloride solution, and dried over anhydrous sodium sulfate. Filtered and concentrated under reduced pressure to obtain 94 mg of product. m/z $[M+H]^+$=415.5

$^1$H NMR (400 MHz, DMSO-d6) ppm 7.55 (s, 1H) 6.76 (s, 1H) 3.82 (d, 2H) 3.65 (s, 2H) 3.22 (t, 2H) 3.05 (q, 4H) 2.95 (t, 1H) 2.46 (br. s., 4H) 1.66 (br. s., 2H) 1.44-1.56 (m, 6H) 1.37 (br. s., 2H) 1.03-1.14 (m, 3H) 0.81 (t, 3H)

In a 25 mL three-neck flask, material IIa (50 mg, 0.12 mmol), 1-ethyl-3(3-dimethylpropylamine)carbodiimide (34.5 mg, 0.18 mmol), and 1-hydroxybenzotriazole (23.67 mg, 0.18 mmol) and N,N-diisopropylethylamine (77.89 mg, 0.6 mmol) was mixed, dissolved in 3 mL N,N-dimethylformamide, and stirred well; material 3-(Aminomethyl)-4,6-dimethylpyridine-2(1H)-one hydrochloride (24.9 mg, 0.13 mmol) was added, the reaction was carried out at room temperature while stirring, and terminated once the disappearance of the starting point IIa was detected by thin layer chromatography. Excess water was added to the reaction solution, and the mixture was extracted with a mixed solvent of dichloromethane and methanol. The organic phases were combined, washed with water then saturated sodium chloride solution. After drying over anhydrous sodium sulfate, filtering, and concentrating under reduced pressure, the remaining residue was purified by a dichloromethane-methanol eluent system to obtain 30.1 mg of a white solid in yield of 47.0%.

m/z $[M+H]^+$=549.6

$^1$H NMR (400 MHz, DMSO-d6) ppm 11.51 (s, 1H) 8.17 (t, 1H) 7.39 (s, 1H) 6.47 (s, 1H) 5.86 (s, 1H) 4.32 (d, 2H) 3.83 (d, 2H) 3.53 (s, 2H) 3.21 (t, 2H) 3.04 (d, 2H) 2.94 (br. s., 1H) 2.79 (d, 2H) 2.38 (br. s., 4H) 2.23 (s, 3H) 2.08-2.14 (m, 3H) 1.65 (d, 2H) 1.44-1.56 (m, 6H) 1.36 (d, 2H) 1.02 (t, 3H) 0.81 (t, 3H).

What is claimed is:
1. A method for preparing a benzofuran derivative represented by formula IV, wherein a compound represented by formula IV is prepared by reacting of a compound represented by formula VI with a compound represented by formula V,

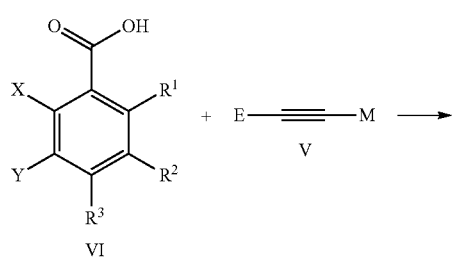

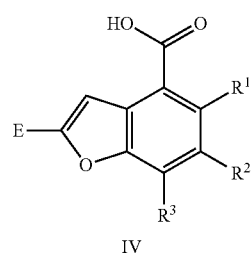

wherein X and Y are each independently selected from fluorine, chlorine, bromine, iodine, —OS(O)$_2$ alkyl and —OS(O)$_2$ aryl, preferably iodine and bromine;

R$^1$, R$^2$, R$^3$ are each identical or different, and are each independently selected from the group consisting of hydrogen atom, halogen, alkyl, haloalkyl, alkoxy, haloalkoxy, amino, nitro, hydroxyl, cyano, cycloalkyl, heterocyclyl, aryl, heteroaryl, —OR$^4$, —C(O)R$^4$, —C(O)OR$^4$, —OS(O)$_2$alkyl, and —OS(O)$_2$aryl, —S(O)$_m$R$^4$, —S(O)$_m$NR$^5$R$^6$ and —(CH$_2$)xR$^a$, wherein alkyl, haloalkyl, heterocyclyl, aryl and heteroaryl are each independently and optionally substituted by one or more substituents selected from the group consisting of alkyl, haloalkyl, halogen, amino, nitro, cyano, hydroxyl, alkoxy, haloalkoxy, hydroxyalkyl, cycloalkyl, heterocyclyl, aryl and heteroaryl;

E is selected from the group consisting of hydrogen atom, halogen, alkyl, haloalkyl, alkoxy, haloalkoxy, nitro, cyano, cycloalkyl, heterocyclyl, aryl, heteroaryl, —OR$^4$, —C(O)R$^4$, —C(O)OR$^4$, —OS(O)$_2$alkyl, and —OS(O)$_2$aryl, —S(O)$_m$R$^4$, —S(O)$_m$NR$^5$R$^6$ and —(CH$_2$)xR$^a$, wherein the alkyl, haloalkyl, heterocyclyl, aryl and heteroaryl are each independently and optionally substituted by any one or more substituents selected from the group consisting of alkyl, haloalkyl, halogen, amino, nitro, cyano, hydroxyl, alkoxy, haloalkoxy, hydroxyalkyl, cycloalkyl, heterocyclyl, aryl and heteroaryl;

R$^a$ is selected from the group consisting of halogen, cycloalkyl, heterocyclyl and —NR$^5$R$^6$, wherein the cycloalkyl and heterocyclyl are independently and optionally substituted by one or more substituents selected from the group consisting of alkyl, haloalkyl, halogen, amino, nitro, cyano, hydroxyl, alkoxy, haloalkoxy, hydroxyalkyl, cycloalkyl, heterocyclyl, aryl and heteroaryl;

R$^4$ is selected from the group consisting of hydrogen atom, alkyl, haloalkyl, alkoxy, hydroxyalkyl, hydroxyl, amino, cycloalkyl, heterocyclyl, aryl and heteroaryl;

R$^5$ and R$^6$ are each identical or different, and are each independently selected from the group consisting of hydrogen atom, alkyl, alkoxy, hydroxyalkyl, hydroxyl, amino, carboxylate, cycloalkyl, heterocyclyl, aryl and heteroaryl, wherein the alkyl, amino, cycloalkyl, heterocyclyl, aryl and heteroaryl are each independently and optionally substituted by one or more substituents selected from the group consisting of alkyl, halogen, hydroxyl, amino, carboxylate, nitro, cyano, alkoxy, hydroxyalkyl, cycloalkyl, heterocyclyl, aryl and heteroaryl;

M is selected from carboxyl, hydrogen and silicyl, preferably hydrogen;

m is 0, 1 or 2;

x is 0, 1, 2 or 3.

2. The method according to claim 1, wherein the reacting of the compound represented by formula VI with the compound represented by formula V is performed under the action of at least one metal catalyst and/or at least one alkaline substance, wherein the metal catalyst is selected from a metal palladium catalyst, a metal zinc catalyst, a metal copper catalyst and a metal nickel catalyst, preferably a metal copper catalyst, and more preferably a monovalent metal copper catalyst, wherein the alkaline substance is selected from the group consisting of KHCO$_3$, NaHCO$_3$, Na$_2$CO$_3$, Ba(OH)$_2$, K$_3$PO$_4$, Cs$_2$CO$_3$, K$_2$CO$_3$, KF, CsF, KCN, NaCN, NaOH, KOH, Et$_3$N, DIPEA, DABCO, NaOMe, NaOEt, $^t$BuOK, $^t$BuONa, NaH, DBU, TMG, LHMDS, NaHMDS, n-BuLi, sodium tert-pentoxide, diethylamine and dicyclohexylamine, preferably $^t$BuOK and $^t$BuONa.

3. The method according to claim 2, wherein the reaction solvent is one or more selected from the group consisting of dimethylformamide, 1-methyl-2-pyrrolidone, tetrahydrofuran, methyltetrahydrofuran, dioxane, toluene, xylene, dimethylsulfoxide, diethyl ether, isopropyl ether, methyl tert-butyl ether, acetonitrile, propionitrile, isopropanol, propanol, ethanol, methanol and water.

4. The method according to claim 2, wherein the reaction is carried out under the protection of an inert gas selected from nitrogen, argon and helium, preferably argon.

5. The method according to claim 1 which comprises the step of a compound represented by formula IVa is prepared by reacting of a compound represented by formula VIa with a compound represented by formula Va,

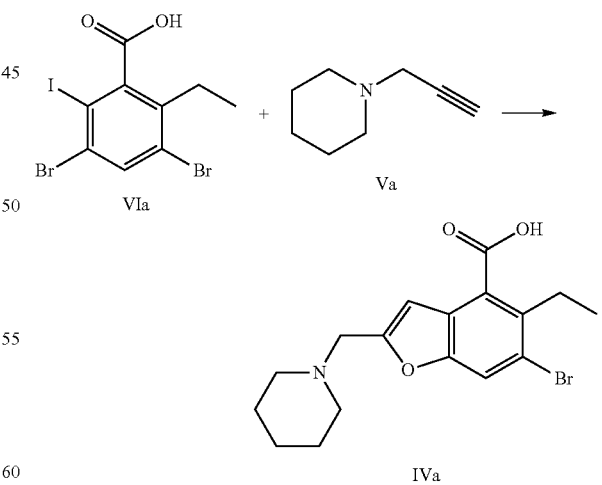

6. The method for preparing the compound represented by formula IVa according to claim 5, which further comprises preparing the compound represented by formula VIa by using a compound represented by formula VIIa under the action of a brominating reagent and at least one acid,

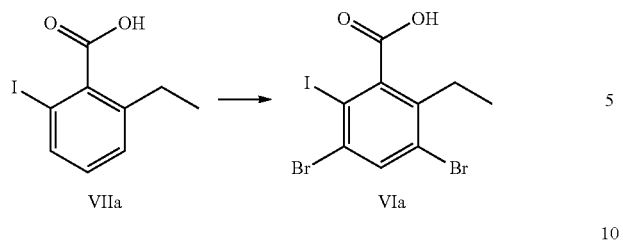

wherein the brominating reagent is selected from the group consisting of HBr, $Br_2$, NBS, DBDMH, HOBr, AcOBr, $CF_3COOBr$, $NH_4Br$, TBBDA, PBBS and tribromoisocyanurate, preferably NBS or DBDMH, wherein the acid is selected from the group consisting of $AlCl_3$, $SbCl_5$, $FeCl_3$, $FeBr_3$, $SnCl_4$, $TiCl_4$, $ZnCl_2$, $BF_3$, acetic acid, sulfuric acid, hydrochloric acid and trifluoroacetic acid, preferably sulfuric acid or trifluoroacetic acid.

* * * * *